United States Patent
Mulier et al.

(10) Patent No.: US 6,623,515 B2
(45) Date of Patent: *Sep. 23, 2003

(54) STRAIGHT NEEDLE APPARATUS FOR CREATING A VIRTUAL ELECTRODE USED FOR THE ABLATION OF TISSUE

(75) Inventors: Peter M. J. Mulier, Stillwater, MN (US); Michael F. Hoey, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/941,458

(22) Filed: Aug. 29, 2001

(65) Prior Publication Data

US 2002/0035387 A1 Mar. 21, 2002

Related U.S. Application Data

(63) Continuation of application No. 09/347,636, filed on Jul. 6, 1999, now Pat. No. 6,302,903.
(60) Provisional application No. 60/091,952, filed on Jul. 7, 1998.

(51) Int. Cl.$^7$ .................................................. A61F 7/00
(52) U.S. Cl. .......................................... 607/105; 606/41
(58) Field of Search .................... 606/41, 45, 48–50; 607/101–105; 604/22, 113, 114; 128/898

(56) References Cited

U.S. PATENT DOCUMENTS

| | | | |
|---|---|---|---|
| 5,403,311 A | 4/1995 | Abele et al. | 606/49 |
| 5,431,649 A | 7/1995 | Mulier et al. | 606/41 |
| 5,433,708 A | 7/1995 | Nichols et al. | 604/113 |
| 5,437,662 A | 8/1995 | Nardella | 606/40 |
| 5,458,597 A * | 10/1995 | Edwards et al. | 606/41 |
| 5,462,521 A * | 10/1995 | Brucker et al. | 604/20 |
| 5,542,928 A | 8/1996 | Evans et al. | 604/113 |
| 5,584,872 A | 12/1996 | LaFontaine et al. | 607/116 |
| 5,609,151 A | 3/1997 | Mulier | 128/642 |
| 5,653,692 A | 8/1997 | Masterson et al. | 604/113 |
| 5,697,281 A | 12/1997 | Eggers et al. | 604/114 |
| 5,697,536 A | 12/1997 | Eggers et al. | 604/114 |
| 5,697,909 A | 12/1997 | Eggers et al. | 604/114 |
| 5,697,927 A | 12/1997 | Imran et al. | 606/41 |
| 5,725,524 A | 3/1998 | Mulier et al. | 606/41 |
| 5,800,482 A | 9/1998 | Pomeranz et al. | 607/101 |
| 5,800,486 A | 9/1998 | Thome et al. | 607/105 |
| 5,807,395 A | 9/1998 | Mulier et al. | 606/41 |
| 5,876,398 A | 3/1999 | Mulier et al. | 606/41 |
| 5,888,198 A | 3/1999 | Eggers et al. | 604/114 |
| 5,891,095 A | 4/1999 | Eggers et al. | 604/114 |
| 5,897,553 A | 4/1999 | Mulier et al. | 606/41 |
| 5,902,328 A | 5/1999 | LaFontaine et al. | 607/116 |
| 5,906,613 A | 5/1999 | Mulier et al. | 606/41 |
| 5,913,854 A | 6/1999 | Maguire et al. | 606/41 |
| 5,935,123 A * | 8/1999 | Edwards et al. | 606/41 |
| 6,302,903 B1 * | 10/2001 | Mulier et al. | 606/41 |

* cited by examiner

*Primary Examiner*—Michael Peffley
(74) *Attorney, Agent, or Firm*—Daniel W. Latham, Esq.; Timothy A. Czaja, Esq.

(57) ABSTRACT

A surgical apparatus for delivering a conductive fluid to a target site for ablating bodily tissue. The apparatus includes a tube fluidly connected to a source of conductive fluid. The tube defines a proximal portion, a distal portion and a central pathway. The central pathway extends from the proximal portion to the distal portion and is configured to direct flow of conductive fluid to the distal portion. The distal portion is configured for placement at a target site of bodily tissue and forms a helical slot. The helical slot is configured to allow flow of conductive fluid from the central pathway. Following delivery of the conductive fluid, an electrical current is applied to create a virtual electrode for ablating bodily tissue at the target site.

10 Claims, 1 Drawing Sheet

STRAIGHT NEEDLE APPARATUS FOR CREATING A VIRTUAL ELECTRODE USED FOR THE ABLATION OF TISSUE

This application is a continuation of application Ser. No. 09/347,636, filed Jul. 6, 1999 is now U.S. Pat. No. 6,302,403, the teachings of which are incorporated herein by reference, that claims the benefit of U.S. Provisional Application No. 60/091,952, filed on Jul. 7, 1998.

FIELD OF THE INVENTION

The present invention relates generally to an apparatus for creating a virtual electrode. More particularly, the present invention relates to an apparatus for the creation of a virtual electrode that is useful for the ablation of soft tissue and neoplasms.

BACKGROUND OF THE PRESENT INVENTION

The utilization of an electric current to produce an ameliorative effect on a bodily tissue has a long history, reportedly extending back to the ancient Greeks. The effects on bodily tissue from an applied electric current, and thus the dividing line between harmful and curative effects, will vary depending upon the voltage levels, current levels, the length of time the current is applied, and the tissue involved. One such effect resulting from the passage of an electric current through tissue is heat generation.

Body tissue, like all non-superconducting materials, conducts current with some degree of resistance. This resistance creates localized heating of the tissue through which the current is being conducted. The amount of heat generated will vary with the power P deposited in the tissue, which is a function of the product of the square of the current I and the resistance R of the tissue to the passage of the current through it ($P=I^2R$.).

As current is applied to tissue, then, heat is generated due to the inherent resistance of the tissue. Deleterious effects in the cells making up the tissue begin to occur at about 42° Celsius. As the temperature of the tissue increases due to heat generated by the tissue's resistance, the tissue will undergo profound changes and eventually, as the temperature becomes high enough, that is, generally greater than 45° C., the cells will die. The zone of cell death is known as a lesion and the procedure followed to create the lesion is commonly called an ablation. As the temperature increases beyond cell death temperature, complete disintegration of the cell walls and cells caused by boiling off of the tissue's water can occur. Cell death temperatures can vary somewhat with the type of tissue to which the power is being applied, but generally will begin to occur within the range of 45° to 60° C., though actual cell death of certain tissue cells may occur at a higher temperature.

In recent times, electric current has found advantageous use in surgery, with the development of a variety of surgical instruments for cutting tissue or for coagulating blood. Still more recently, the use of alternating electric current to ablate, that is, kill, various tissues has been explored. Typically, current having a frequency from about 3 kilohertz to about 300 gigahertz, which is generally known as radiofrequency or radiofrequency (RF) current, is used for this procedure. Destruction, that is, killing, of tissue using an RF current is commonly known as radiofrequency ablation. Often radiofrequency ablation is performed as a minimally invasive procedure and is thus known as radiofrequency catheter ablation because the procedure is performed through and with the use of a catheter. By way of example, radiofrequency catheter ablation has been used to ablate cardiac tissue responsible for irregular heart beats or arrythmias.

The prior art applications of current to tissue have typically involved applying the current using a "dry" electrode. That is, a metal electrode is applied to the tissue desired to be affected and a generated electric current is passed through the electrode to the tissue. A commonly known example of an instrument having such an operating characteristic is an electrosurgical instrument known as a "bovie" knife. This instrument includes a cutting/coagulating blade electrically attached to a current generator. The blade is applied to the tissue of a patient and the current passes through the blade into the tissue and through the patient's body to a metal base electrode or ground plate usually placed underneath and in electrical contact with the patient. The base electrode is in turn electrically connected to the current generator so as to provide a complete circuit.

As the current from the bovie knife passes from the blade into the tissue, the resistance provided by the tissue creates heat. In the cutting mode, a sufficient application of power through the bovie knife to the tissue causes the fluid within the cell to turn to steam, creating a sufficient overpressure so as to burst the cell walls. The cells then dry up, desiccate, and carbonize, resulting in localized shrinking and an opening in the tissue. Alternatively, the bovie knife can be applied to bleeding vessels to heat and coagulate the blood flowing therefrom and thus stop the bleeding.

As previously noted, another use for electrical instruments in the treatment of the body is in the ablation of tissue. To expand further on the brief description given earlier of the ablation of cardiac tissue, it has long been known that a certain kind of heart tissue known as sino-atrial and atrio-ventricular nodes spontaneously generate an electrical signal that is propagated throughout the heart along conductive pathways to cause it to beat. Occasionally, certain heart tissue will "misfire," causing the heart to beat irregularly. If the errant electrical pathways can be determined, the tissue pathways can be ablated and the irregular heartbeat remedied. In such a procedure, an electrode is placed via a catheter into contact with the tissue and then current is applied to the tissue via the electrode from a generator of RF current. The applied current will cause the tissue in contact with the electrode to heat. Power will continue to be applied until the tissue reaches a temperature where the heart tissue dies, thereby destroying the errant electrical pathway and the cause of the irregular heartbeat.

Another procedure using RF ablation is transurethral needle ablation, or TUNA, which is used to create a lesion in the prostate gland for the treatment of benign prostatic hypertrophy (BPH) or the enlargement of the prostate gland. In a TUNA procedure, a needle having an exposed conductive tip is inserted into the prostate gland and current is applied to the prostate gland via the needle. As noted previously, the tissue of the prostate gland heats locally surrounding the needle tip as the current passes from the needle to the base electrode. A lesion is created as the tissue heats and the destroyed cells may be reabsorbed by the body, infiltrated with scar tissue, or just become non-functional.

While there are advantages and uses for such "dry" electrode instruments, there are also several notable disadvantages. One of these disadvantages is that during a procedure, coagulum—dried blood cells and tissue cells—will form on the electrode engaging the tissue. Coagulum acts as an insulator and effectively functions to prevent current transfer from the blade to the tissue. This coagulum "insulation" can be overcome with more voltage so as to keep the current flowing, but only at the risk of arcing and injuring the patient. Thus, during surgery when the tissue is cut with an electrosurgical scalpel, a build-up of coagulated blood and desiccated tissue will occur on the blade, requiring the blade to be cleaned before further use. Typically, cleaning an electrode/scalpel used in this manner will involve simply scraping the dried tissue from the electrode/ scalpel by rubbing the scalpel across an abrasive pad to remove the coagulum. This is a tedious procedure for the surgeon and the operating staff since it requires the "real" work of the surgery to be discontinued while the cleaning operation occurs. This procedure can be avoided with the use of specially coated blades that resist the build up of coagulum. Such specialty blades are costly, however.

A second disadvantage of the dry electrode approach is that the electrical heating of the tissue creates smoke that is now known to include cancer-causing agents. Thus, preferred uses of such equipment will include appropriate ventilation systems, which can themselves become quite elaborate and quite expensive.

A further, and perhaps the most significant, disadvantage of dry electrode electrosurgical tools is revealed during cardiac ablation procedures. During such a procedure, an electrode that is otherwise insulated but having an exposed, current carrying tip is inserted into the heart chamber and brought into contact with the inner or endocardial side of the heart wall where the ablation is to occur. The current is initiated and passes from the current generator to the needle tip electrode and from there into the tissue so that a lesion is created. Typically, however, the lesion created by a single insertion is insufficient to cure the irregular heartbeat because the lesion created is of an insufficient size to destroy the errant electrical pathway. Thus, multiple needle insertions and multiple current applications are almost always required to ablate the errant cardiac pathway, prolonging the surgery and thus increasing the potential risk to the patient.

This foregoing problem is also present in TUNA procedures, which similarly require multiple insertions of the needle electrode into the prostate gland. Failing to do so will result in the failure to create a lesion of sufficient size otherwise required for beneficial results. As with radiofrequency catheter ablation of cardiac tissue, then, the ability to create a lesion of the necessary size to alleviate BPH symptoms is limited and thus requires multiple insertions of the electrode into the prostate.

A typical lesion created with a dry electrode using RF current and a single insertion will normally not exceed one centimeter in diameter. This small size—often too small to be of much or any therapeutic benefit—stems from the fact that the tissue surrounding the needle electrode tends to desiccate as the temperature of the tissue increases, leading to the creation of a high resistance to the further passage of current from the needle electrode into the tissue, all as previously noted with regard to the formation of coagulum on an electrosurgical scalpel. This high resistance—more properly termed impedance since typically an alternating current is being used—between the needle electrode and the base electrode is commonly measured by the RF current generator. When the measured impedance reaches a predetermined level, the generator will discontinue current generation. Discontinuance of the ablation procedure under these circumstances is necessary to avoid injury to the patient.

Thus, a typical procedure with a dry electrode may involve placing the needle electrode at a first desired location; energizing the electrode to ablate the tissue; continue applying current until the generator measures a high impedance and shuts down; moving the needle to a new location closely adjacent to the first location; and applying current again to the tissue through the needle electrode. This cycle of electrode placement, electrode energization, generator shut down, electrode re-emplacement, and electrode re-energization, will be continued until a lesion of the desired size has been created. As noted, this increases the length of the procedure for the patient. Additionally, multiple insertions increases the risk of at least one of the placements being in the wrong location and, consequently, the risk that healthy tissue may be undesirably affected while diseased tissue may be left untreated. The traditional RF ablation procedure of using a dry ablation therefore includes several patient risk factors that both patient and physician would prefer to reduce or eliminate.

The therapeutic advantages of RF current could be increased if a larger lesion could be created safely with a single positioning of the current-supplying electrode. A single positioning would allow the procedure to be carried out more expeditiously and more efficiently, reducing the time involved in the procedure. Larger lesions can be created in at least two ways. First, simply continuing to apply current to the patient with sufficiently increasing voltage to overcome the impedance rises will create a larger lesion, though almost always with undesirable results to the patient. Second, a larger lesion can be created if the current density, that is, the applied electrical energy, could be spread more efficiently throughout a larger volume of tissue. Spreading the current density over a larger tissue volume would correspondingly cause a larger volume of tissue to heat in the first instance. That is, by spreading the applied power throughout a larger tissue volume, the tissue would heat more uniformly over a larger volume, which would help to reduce the likelihood of generator shutdown due to high impedance conditions. The applied power, then, will cause the larger volume of tissue to be ablated safely, efficiently, and quickly.

Research conducted under the auspices of the assignee of the present invention has focused on spreading the current density throughout a larger tissue volume through the creation, maintenance, and control of a "virtual electrode" within or adjacent to the tissue to be ablated. A virtual electrode can be created by the introduction of a conductive fluid, such as isotonic or hypertonic saline, into or onto the tissue to be ablated. The conductive fluid will facilitate the spread of the current density substantially equally throughout the extent of the flow of the conductive fluid, thus creating an electrode—a virtual electrode—substantially equal in extent to the size of the delivered conductive fluid. RF current can then be passed through the virtual electrode into the tissue.

A virtual electrode can be substantially larger in volume than the needle tip electrode typically used in RF interstitial ablation procedures and thus can create a larger lesion than can a dry, needle tip electrode. That is, the virtual electrode spreads or conducts the RF current density outward from the RF current source—such as a current carrying needle, forceps or other current delivery device—into or onto a larger volume of tissue than is possible with instruments that rely on the use of a dry electrode. Stated otherwise, the creation of the virtual electrode enables the current to flow with reduced resistance or impedance throughout a larger volume of tissue, thus spreading the resistive heating created by the current flow through a larger volume of tissue and thereby creating a larger lesion than could otherwise be created with a dry electrode.

While the efficacy of RF current ablation techniques using a virtual electrode has been demonstrated in several studies, the currently available instruments useful in such procedures lags behind the research into and development of hoped-for useful treatment modalities for the ablation of soft tissue and malignancies.

It would be desirable to have an apparatus capable of creating a virtual electrode for the controlled application of tissue ablating RF electric current to a tissue of interest so as to produce a lesion of desired size and configuration.

SUMMARY OF THE INVENTION

One aspect of the present invention provides a surgical apparatus for delivering a conductive fluid to a target site for ablating bodily tissue. The surgical apparatus includes a tube fluidly connected to a source of conductive fluid. The tube defines a proximal portion, a distal portion and a central pathway. The central pathway extends from the proximal portion to the distal portion and is configured to allow the conductive fluid to flow from the proximal portion to the distal portion. The distal portion is configured for placement at a target site of bodily tissue. Further, the distal portion forms a helical slot. The helical slot is configured to allow flow of conductive fluid outwardly from the central pathway. In one preferred embodiment, the distal portion is substantially straight and forms a needle. During use, the conductive fluid is delivered in a generally uniform fashion from the distal portion via the helical slot. Following delivery, a current is applied to the bolus of distributed conductive fluid, thereby creating a virtual electrode.

Another aspect of the present invention relates to a surgical system for creating a virtual electrode to ablate bodily tissue at a target site. The surgical system comprises a fluid source, a current source, and a surgical instrument. The fluid source maintains a supply of conductive fluid. The current source is configured to selectively supply an electrical current. Finally, the surgical instrument includes a tube and an electrode. The tube is fluidly connected to the fluid source and defines a proximal portion, a distal portion and a central pathway. The central pathway extends from the proximal portion to the distal portion for directing the conductive fluid to the distal portion. In this regard, the distal portion is configured for placement at a target site and forms a helical slot. The helical slot is configured to allow flow of the conductive fluid outwardly from the central pathway. Finally, the electrode is connected to the current source for applying a current conductive fluid delivered from the distal portion of the tube. Thus, upon applying the current, a virtual electrode is created.

DETAILED DESCRIPTION OF THE PREFERRED EMBODIMENTS

Figure 1:
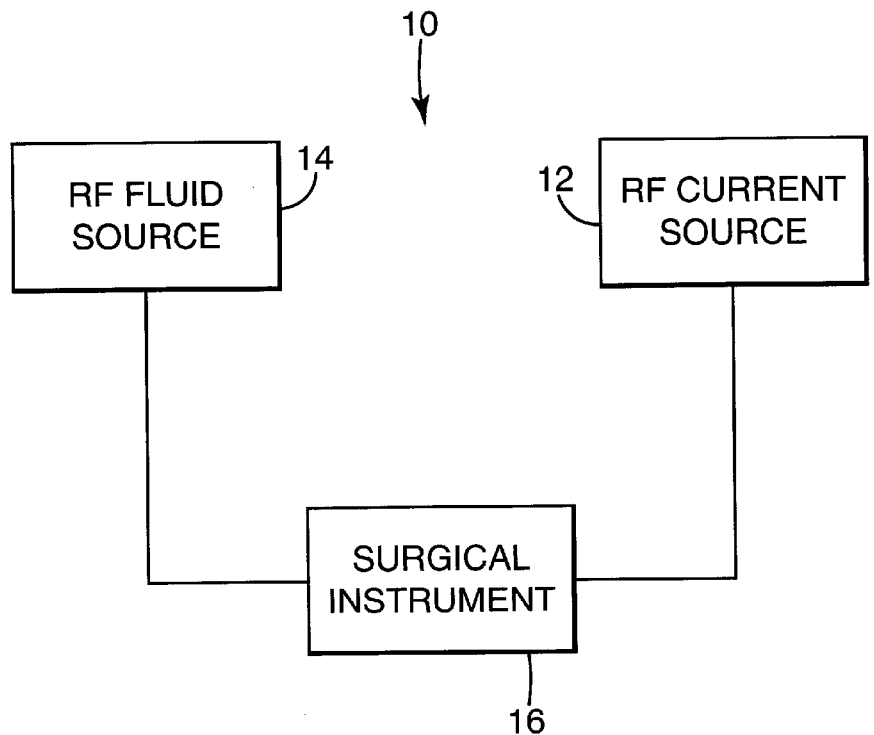
FIG. 1 is a block diagram of a surgical system for creating a virtual electrode to ablate bodily tissue in accordance with the present invention.

FIG. 1 illustrates in block form a surgical system 10 for RF ablation useful with the present invention. The surgical system 10 includes a current source of radio-frequency alternating electric current 12, a fluid source of RF ablating fluid 14, including but not limited to saline and other conductive solutions, and a surgical instrument 16, for delivering the RF current and the ablation fluid to a tissue site (not shown) for ablation purposes. In one preferred embodiment, the surgical instrument 16 is connected to the current source 12 and the fluid source 14. It will be understood that the current source 12 and the fluid source 14 may be combined into a single operational structure controlled by an appropriate microprocessor for a controlled delivery of ablating fluid and a controlled application of RF current, both based upon measured parameters such as, but not limited to, flow rate, tissue temperature at the ablation site and at areas surrounding the ablation site, impedance, the rate of change of the impedance, the detection of arcing between the surgical instrument and the tissue, the time period during which the ablation procedure has been operating, and additional factors as desired.

Figure 2:
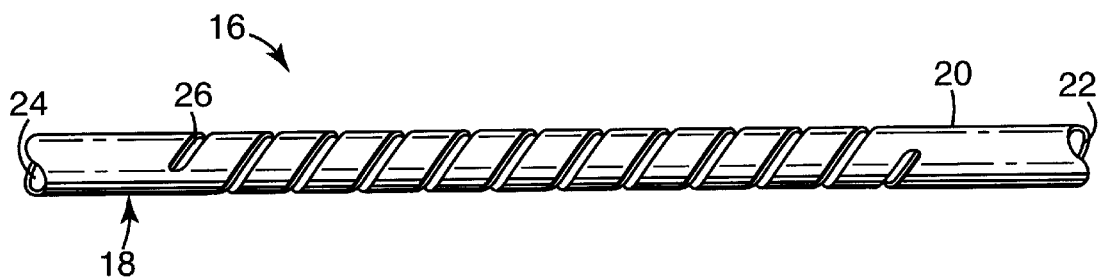
FIG. 2 is an enlarged, side view of a portion of a surgical instrument in accordance with the present invention.

The surgical instrument 16 may assume a wide variety of forms. In this regard, one preferred embodiment of a surgical instrument 16 is shown in FIG. 2. The surgical instrument 16 comprises an elongated needle tube 18, a distal portion of which is depicted in FIG. 2 for ease of illustration. In a preferred embodiment, the needle tube 18 is similar in basic construction to a needle electrode device previously described. However, the needle tube 18 shown in FIG. 2 is tubular in form, having an outer surface 20 and an inner surface 22. The inner surface 22 defines a central fluid pathway 24.

In one preferred embodiment, the needle tube 10 has a substantially straight or linear configuration. The distal portion of the needle tube 18 forms a helical slot 26 cut or otherwise machined from the outer surface 20 through to the inner surface 22. The slot 26 is configured to allow a desired amount of conductive fluid, otherwise supplied to the needle tube 18 by the fluid source 14 (FIG. 1), to leak from the flow path 24 outwardly into tissue (not shown) during an ablation procedure. As shown, the slot 26 preferably has a substantially uniform pitch and axial width, though the pitch may vary as desired and the slot 26 widths may vary as desired along the length of the needle tube 18 to provide the amount of fluid distribution as desired in the direction desired within the tissue to be ablated. As noted, although only a single slot 26 is shown, a plurality of concentric parallel grooves may instead be provided.

As with the needle electrode previously described, the surgical instrument 16 similarly preferably includes one or more electrodes. With reference to FIG. 2, the electrode may be integral with the material comprising the needle tube 18, or may be a separate element. In this regard, the electrode may be formed along the slot 26, or may instead be disposed adjacent the slot 26 either distal or proximal thereto.

It will be understood that while the surgical instrument 16 is shown in FIG. 1 as being connected to both the current source 12 and the fluid source 14 in the form of a single straight or coiled needle having an exposed end and a fluid flow path there through to deliver both fluid and current to the target tissue for ablation purposes, the present system is not so limited but could include separate needles. For example, a separate needle could be used to deliver the current and a separate needle or needles could be used to deliver fluid to the target tissue. In addition, the application of the present system is not limited to the use of straight needles or helical needles as surgical instruments but could find use with any type of instrument wherein a conductive solution is delivered to a tissue and an RF current is applied to the tissue through the conductive fluid. Such instruments thus would include straight needles, helical needles, forceps, roller balls, instruments for the treatment of vascular disorders, and any other instrument generally useful in treating disorders with RF current.

Although the present invention has been described with reference to preferred embodiments, workers skilled in the art will recognize that changes may be made in form and detail without departing from the spirit and scope of the invention.

What is claimed is:

1. A method of ablating bodily tissue of a patient, the method comprising:

providing a surgical apparatus including a tube having a needle and an electrode at a distal portion thereof and a central pathway, the needle forming a helical slot along at least a portion of a length of the needle, the slot being in fluid communication with the central pathway;

penetrating the bodily tissue with the needle, such that at least a portion of the slot is within the tissue;

delivering conductive fluid to the bodily tissue via the slot; and applying RE energy to the delivered conductive fluid via the electrode to ablate the bodily tissue.

2. The method of claim 1, further comprising:

delivering conductive fluid during the step of applying RF energy.

3. The method of claim 1, wherein the step of delivering conductive fluid includes distributing conductive fluid into the bodily tissue.

4. The method of claim 1, wherein the step of delivering conductive fluid includes leaking conductive fluid outwardly from the central pathway.

5. The method of claim 1, wherein the step of delivering conductive fluid occurs after the step of penetrating the bodily tissue.

6. The method of claim 1, further comprising:

controlling the delivery of conductive fluid and the application of RE energy based upon a measured parameter.

7. The method of claim 1, further comprising:

fluidly connecting a proximal end of that central pathway to a source of conductive fluid.

8. The method of claim 1, further comprising:

electrically connecting the electrode to an RF energy source.

9. The method of claim 1, wherein the tube includes a plurality of slots.

10. The method of claim 1, wherein the needle and the electrode are integrally formed.

* * * * *